(12) United States Patent
Mickiewicz et al.

(10) Patent No.: US 9,949,767 B2
(45) Date of Patent: Apr. 24, 2018

(54) METHODS AND DEVICES FOR MANIPULATING A VERTEBRA

(71) Applicant: DePuy Synthes Products, Inc., Raynham, MA (US)

(72) Inventors: Christopher Mickiewicz, Bridgewater, MA (US); John R. Cournoyer, Norfolk, MA (US); James R. Donahue, East Falmouth, MA (US); Richard W. Fournier, New Bedford, MA (US); SeungKyu Daniel Kwak, Grafton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 72 days.

(21) Appl. No.: 15/098,615

(22) Filed: Apr. 14, 2016

(65) Prior Publication Data
US 2016/0228154 A1 Aug. 11, 2016

Related U.S. Application Data

(63) Continuation of application No. 12/887,742, filed on Sep. 22, 2010, now Pat. No. 9,339,308.

(60) Provisional application No. 61/245,108, filed on Sep. 23, 2009.

(51) Int. Cl.
*A61B 17/70* (2006.01)

(52) U.S. Cl.
CPC ........ *A61B 17/7047* (2013.01); *A61B 17/708* (2013.01)

(58) Field of Classification Search
CPC combination set(s) only.
See application file for complete search history.

(56) References Cited

U.S. PATENT DOCUMENTS

| | | | |
|---|---|---|---|
| 4,360,012 A * | 11/1982 | McHarrie | ............ A61B 17/171 606/54 |
| 4,950,269 A | 8/1990 | Gaines, Jr. | |
| 5,129,899 A | 7/1992 | Small et al. | |
| 5,261,913 A | 11/1993 | Marnay | |
| 5,334,203 A * | 8/1994 | Wagner | .............. A61B 17/7052 24/396 |
| 5,499,983 A | 3/1996 | Hughes | |

(Continued)

OTHER PUBLICATIONS

International Search Report and Written Opinion for PCT/US2010/049775 dated Sep. 22, 2010 (10 pages).

(Continued)

*Primary Examiner* — Jan Christopher Merene
(74) *Attorney, Agent, or Firm* — Nutter McClennen & Fish LLP

(57) ABSTRACT

Methods and devices are provided for manipulating a vertebra. In one embodiment, a surgical device can include a frame configured to couple two or more surgical instruments attached to one or more vertebrae. Coupling the two or more surgical instruments together, the frame and/or at least one of the surgical instruments can be manipulated to move at least one of the surgical instruments, thereby effecting movement at least one of the vertebra or vertebrae to which the surgical instruments coupled to the frame are attached. In this way, the surgical device can be used to facilitate rotation of a vertebra relative to another vertebra to correct the angular relationship of the vertebrae.

12 Claims, 13 Drawing Sheets

(56) References Cited

U.S. PATENT DOCUMENTS

| | | | |
|---|---|---|---|
| 5,522,816 A | 6/1996 | Dinello et al. | |
| 5,591,235 A | 1/1997 | Kuslich | |
| 5,702,393 A * | 12/1997 | Pfaifer | A61B 17/7049 606/250 |
| 5,976,133 A | 11/1999 | Kraus et al. | |
| 6,287,309 B1 | 9/2001 | Baccelli et al. | |
| 6,340,361 B1 | 1/2002 | Kraus et al. | |
| 6,652,523 B1 | 11/2003 | Evrard et al. | |
| 7,179,261 B2 | 2/2007 | Sicvol et al. | |
| 7,588,585 B2 | 9/2009 | Gold et al. | |
| 7,591,836 B2 | 9/2009 | Dick et al. | |
| 7,708,736 B2 | 5/2010 | Mullaney | |
| 7,951,175 B2 | 5/2011 | Chao et al. | |
| 8,888,777 B2 | 11/2014 | Mullaney | |
| 9,220,541 B1 * | 12/2015 | Dant | A61B 17/7049 |
| 9,339,308 B2 | 5/2016 | Mickiewicz et al. | |
| 2003/0045875 A1 | 3/2003 | Bertranou et al. | |
| 2003/0114852 A1 | 6/2003 | Biedermann et al. | |
| 2004/0092931 A1 | 5/2004 | Taylor et al. | |
| 2006/0200131 A1 | 9/2006 | Chao et al. | |
| 2006/0200132 A1 | 9/2006 | Chao et al. | |
| 2006/0229605 A1 | 10/2006 | Olsen | |
| 2006/0271050 A1 | 11/2006 | Piza Vallespir | |
| 2007/0213715 A1 | 9/2007 | Bridwell et al. | |
| 2007/0213716 A1 | 9/2007 | Lenke et al. | |
| 2007/0231059 A1 | 10/2007 | Mullaney | |
| 2008/0086130 A1 | 4/2008 | Lake et al. | |
| 2009/0018541 A1 | 1/2009 | Lavi | |
| 2009/0062857 A1 | 3/2009 | Ramsay et al. | |
| 2009/0281579 A1 | 11/2009 | Weaver et al. | |
| 2010/0063544 A1 | 3/2010 | Butler | |
| 2010/0312279 A1 * | 12/2010 | Gephart | A61B 17/3421 606/264 |
| 2011/0077689 A1 | 3/2011 | Mickiewicz et al. | |
| 2014/0277198 A1 | 9/2014 | Stad | |

OTHER PUBLICATIONS

International Preliminary Report on Patentability dated Apr. 5, 2012 for Application No. PCT/2010/049775 (8 Pages).

* cited by examiner

*FIG. 8A*
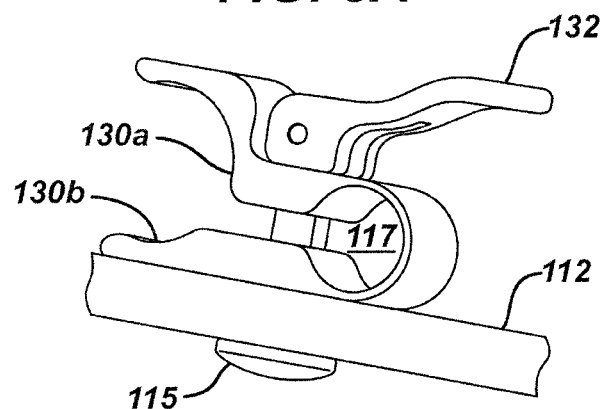
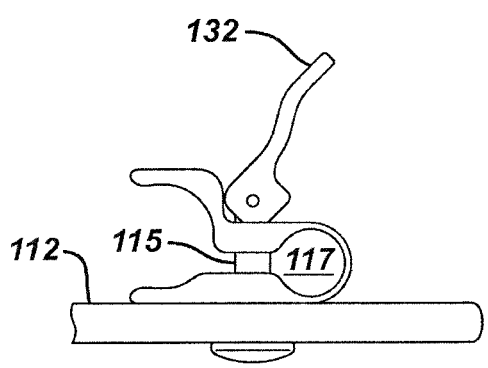
*FIG. 8B*
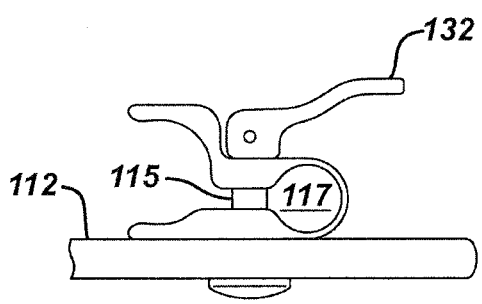
*FIG. 8C*
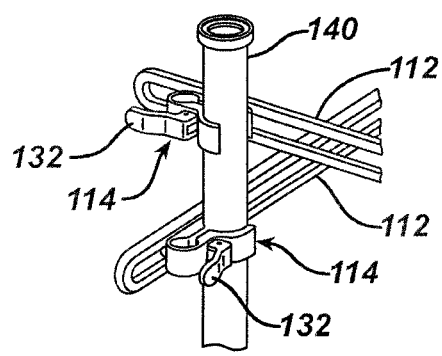
*FIG. 8D*

METHODS AND DEVICES FOR MANIPULATING A VERTEBRA

CROSS REFERENCE TO RELATED APPLICATIONS

The present application is a continuation of U.S. application Ser. No. 12/887,742 filed Sep. 22, 2010, now U.S. Pat. No. 9,339,308, which claims the priority of U.S. Provisional Application No. 61/245,108 filed Sep. 23, 2009, each of which is hereby incorporated by reference in its entirety.

FIELD

The present application relates to methods and devices for manipulating a vertebra.

BACKGROUND

In spinal deformity surgical procedures, the curvature of the spine, for example, the coronal curvature and/or the sagittal curvature of the spine, can be corrected by the implantation of a construct of bone anchors, e.g., hooks, bone screws, etc., and spinal fixation elements, e.g., rods, tethers, etc. In addition to correcting the curvature of the spine, the angular relationship of one or more vertebrae relative to other vertebrae can also be corrected. Conventional surgical procedures for corrected the angular relationship of a vertebra involve rotating the spinal fixation element connected to the vertebra by a bone anchor. In the case of constructs including a spinal rod, this procedure is typically referred to as rod derotation. Rod derotation can place significant stress on the interface between the bone anchors connected to the rotated spinal rod and the vertebra in which each bone anchor is implanted. This stress can cause a failure of one or more of the bone anchors or vertebrae.

Accordingly, there remains a need for methods and devices for manipulating a vertebra.

SUMMARY

In general, methods and devices are provided for manipulating a vertebra. In one embodiment, a surgical device is provided that includes a frame having a longitudinal axis extending between opposed first and second ends, and a clamping mechanism having a central axis and being selectively movable between a secured configuration and an unsecured configuration. The clamping mechanism includes a base portion configured to be selectively positioned and secured at a desired location on the frame along the longitudinal axis of the frame between the first and second ends of the frame, and a clamping portion, disposed opposite the base portion, configured to selectively engage an elongate tubular element at a desired location along a longitudinal axis of the tubular element. The clamping mechanism is configured to rotate about the central axis thereof relative to the frame when the clamping mechanism is in the unsecured configuration.

The device can have any number of variations. For example, the device can also include at least one additional clamping mechanism. For another example, the clamping portion can be substantially c-shaped, which can include an arc equal to or greater than about 180°. For yet another example, the clamping portion can include a closed loop. For still another example, the clamping mechanism can be removably and replaceably mounted to the frame. For another example, at least the clamping portion of the clamping mechanism can be configured to move relative to the frame in a direction substantially perpendicular to the longitudinal axis of the frame. For yet another example, the base portion and the clamping portion can be integrally formed. For still another example, a distal end of the elongate tubular member can be configured to releasably mate to a bone anchor. For another example, the clamping mechanism in the unsecured configuration can be movable along the longitudinal axis of the frame and can be movable along the longitudinal axis of the elongate tubular element, and in the secured configuration can be secured at the desired location on the frame, can be secured at the desired location along the longitudinal axis of the elongate tubular element, and can not be rotatable relative to the frame about the central axis thereof. The clamping mechanism can be movable along substantially an entire longitudinal length of the frame between the opposed first and second ends. The clamping mechanism can includes a cam that can be actuated by a movable lever and be configured to move the clamping mechanism between the unsecured configuration and the secured configuration. The clamping mechanism can include a rotatable knob configured to effect movement of the clamping mechanism between the unsecured configuration and the secured configuration.

In another aspect, a surgical system is provided that includes a frame having a longitudinal axis extending between opposed first and second ends, and a first clamping mechanism having a central axis. The first clamping mechanism includes a base portion configured to be selectively positioned and secured at a desired location on the frame along the longitudinal axis of the frame between the first and second ends of the frame, and a clamping portion, disposed opposite the base portion, configured to selectively and releasably engage an elongate shaft of a first instrument at a desired location along a longitudinal axis of the elongate shaft. The first clamping mechanism has an unsecured configuration in which the first clamping mechanism is rotatable about the central axis thereof relative to the frame and is movable relative to the elongate shaft along the longitudinal axis of the elongate shaft, and has a secured configuration in which the first clamping mechanism is not rotatable about the central axis thereof relative to the frame and is fixed at the desired location along the longitudinal axis of the elongate shaft.

The system can have any number of variations. For example, the clamping portion can be substantially c-shaped, and the c-shaped portion can extend radially outward from the frame. For another example, the first clamping mechanism in the unsecured configuration can be selectively positionable at the desired location on the frame, and the first clamping mechanism in the secured configuration can be secured at a fixed longitudinal position along the longitudinal axis of the frame at the desired location on the frame. For yet another example, the first clamping mechanism can include a cam that can be actuated by a movable lever and be configured to move the first clamping mechanism from the unsecured configuration to the secured configuration. The cam can be configured to move the first clamping mechanism from the secured configuration to the unsecured configuration. For still another example, the first clamping mechanism can include a rotatable knob configured to effect movement of the first clamping mechanism from the unsecured configuration to the secured configuration. The rotatable knob can be configured to effect movement of the first clamping mechanism from the secured configuration to the unsecured configuration. For another example, the first clamping mechanism can be removable from the frame. For yet another example, the first clamping mechanism can not be removable from the frame.

For another example, the system can also include a second clamping mechanism configured to be selectively positioned at a desired location on the frame along the longitudinal axis of the frame, and configured to releasably engage an elongate shaft of a second instrument. The second clamping mechanism has an unlocked configuration in which the second clamping mechanism is rotatable relative to the frame and is movable relative to the elongate shaft of the second instrument along a longitudinal axis extending between proximal and distal ends of the elongate shaft of the second instrument, and has a locked configuration in which the second clamping mechanism is not rotatable relative to the frame and is at a fixed longitudinal position along the longitudinal axis extending between the proximal and distal ends of the elongate shaft of the second instrument. The second clamping mechanism can be removable or not be removable from the frame. The system can further include at least one additional clamping mechanism configured to be selectively positioned at a desired location on the frame along the longitudinal axis of the frame, each additional clamping mechanism being configured to releasably engage an elongate shaft of an additional instrument configured to releasably mate to a bone anchor inserted in the vertebra. Each additional clamping mechanism has an unlocked configuration in which it is rotatable relative to the frame and is movable relative to the elongate shaft of the additional instrument along a longitudinal axis extending between proximal and distal ends of the elongate shaft of the second instrument, and has a locked configuration in which it is not rotatable relative to the frame and is at a fixed longitudinal position along the longitudinal axis extending between the proximal and distal ends of the elongate shaft of the additional instrument.

In another embodiment, a surgical system is provided that includes a plurality of bone anchors, at least one spinal fixation element configured to be seated in at least one of the bone anchors, a frame having a longitudinal axis extending between opposed first and second ends, and a clamping mechanism having a central axis and being selectively movable between a secured configuration and an unsecured configuration. The clamping mechanism includes a base portion configured to be selectively positioned and secured at a desired location on the frame along the longitudinal axis of the frame between the first and second ends of the frame, and a clamping portion, disposed opposite the base portion, configured to selectively engage an elongate tubular element at a desired location along a longitudinal axis of the tubular element. The elongate tubular element is configured to releasably mate to one of the bone anchors, and the clamping mechanism is configured to rotate about the central axis thereof relative to the frame when the clamping mechanism is in the unsecured configuration.

In another aspect, a surgical method for manipulating a vertebra is provided that includes connecting a first bone anchor to a first vertebra, connecting a second bone anchor to a second vertebra, positioning a spinal rod in a receiving member of the first bone anchor and in a receiving member of the second bone anchor, connecting a first instrument to the first bone anchor, connecting a second instrument to the second bone anchor, coupling a frame to the first instrument by selectively engaging a first clamping mechanism coupled to the frame at a desired location along a longitudinal axis of the first instrument, the first clamping mechanism being selectively rotatable about a central axis of the first clamping mechanism relative to the frame, coupling the frame to the second instrument by selectively engaging a second clamping mechanism coupled to the frame at a desired location along a longitudinal axis of the second instrument, the second clamping mechanism being selectively rotatable about a central axis of the second clamping mechanism relative to the frame, and moving the frame to manipulate the first instrument and the second instrument to rotate the first vertebra and the second vertebra relative to one another.

The method can vary in any number of ways. For example, the method can include, prior to coupling the frame to the first instrument, adjusting a position of the first clamping mechanism along a longitudinal axis of the frame between first and second opposed ends of the frame.

In another embodiment, a surgical method for manipulating a vertebra is provided that includes positioning a first clamp member at a first location between opposed first and second ends of a frame, positioning a second clamp member at a second location between the opposed ends of the frame, positioning the first clamp member at a first desired longitudinal location between opposed proximal and distal second ends of a first instrument, the distal end of the first instrument being mated to a first bone anchor, positioning the second clamp member at a second desired longitudinal location between opposed proximal and distal ends of a second instrument, the distal end of the second instrument being mated to a second bone anchor, actuating a first actuator integral with the first clamp member to fix the first clamp member at the first location and at the first desired longitudinal location, and actuating a second actuator integral with the second clamp member to fix the second clamp member at the second location and at the second desired longitudinal location.

The method can have any number of variations. For example, the method can include, prior to positioning the first clamp member at the first location, releasably attaching the first clamp member to the frame. For another example, the method can include prior to actuating the first actuator, rotating the first clamp member about a central axis of the first clamp member relative to the frame. For yet another example, the first and second bone anchors can be inserted in a vertebral body. For still another example, the first and second bone anchors are each inserted in a different vertebral body. The method can also include, after actuating the first and second actuators, moving the frame to move the different vertebral bodies relative to one another.

BRIEF DESCRIPTION OF THE DRAWINGS

Methods, devices, and systems described herein will be more fully understood from the following detailed description taken in conjunction with the accompanying drawings, in which:

FIG. 8A is a perspective view of another embodiment of a clamping mechanism attached to a frame in a secured configuration;

FIG. 8B is a side, partially transparent view of the clamping mechanism and frame of FIG. 8A with the clamping mechanism in an unsecured configuration;

FIG. 8C is a side, partially transparent view of the clamping mechanism and frame of FIG. 8A with the clamping mechanism in an secured configuration;

FIG. 8D is a perspective view of two clamping mechanisms and frames of FIG. 8A coupled to a surgical instrument with the clamping mechanisms in secured configurations;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for manipulating a vertebra. Generally, a surgical device can include a rack, frame, or connector, generally referred to herein as a "frame," configured to couple two or more surgical instruments attached to one or more vertebrae. Coupling the two or more surgical instruments together, the frame and/or at least one of the surgical instruments can be manipulated to move at least one of the surgical instruments, thereby effecting movement at least one of the vertebra or vertebrae to which the surgical instruments coupled to the frame are attached. In this way, the surgical device can be used to facilitate rotation of a vertebra relative to another vertebra to correct the angular relationship of the vertebrae.

The frame can be configured to couple two or more surgical instruments via two or more clamping mechanisms movably attached to the frame. At least one of the clamping mechanisms can be configured to translate longitudinally along a longitudinal length of the frame to allow for x-axis or horizontal adjustment of the clamping mechanism, to radially move relative to the frame to allow for z-axis or depth adjustment of the clamping mechanism, and/or to be positionable at any location along a longitudinal length of the surgical instrument to provide flexibility in y-axis or vertical positions of the clamping mechanism relative to the surgical instrument. In this way, the clamping mechanisms can be positioned in a wide variety of positions to most securely attach to surgical instruments, which can correspondingly be positioned in a wide variety of positions relative to a patient's body. At least one of the clamping mechanisms can be configured as a modular component removable from and replaceable on the frame to allow for any number of clamping mechanisms to be selectively coupled to the frame as desired for a particular surgical application using a plurality of surgical instruments. Modular components can also allow for the frame to be free of unused clamping mechanisms, thereby providing increased space for surgical maneuverability and/or visibility.

Figure 1:
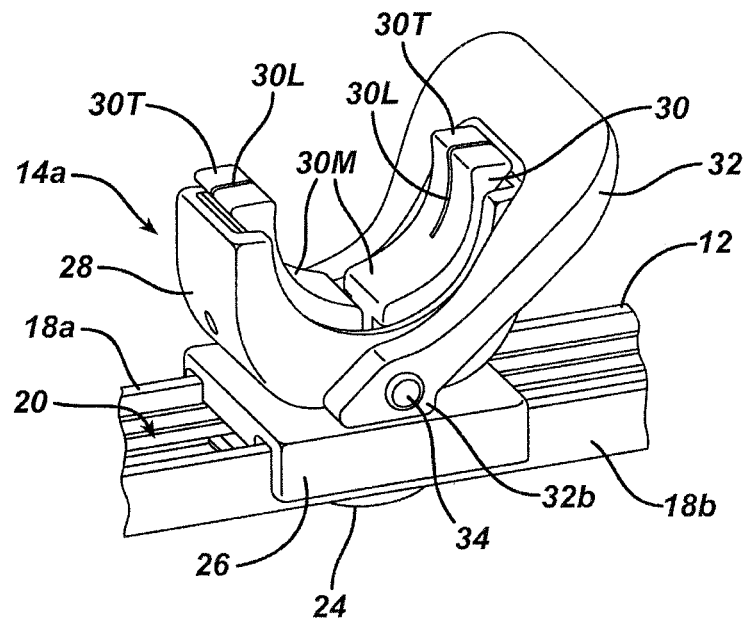
FIG. 1 is a perspective view of one embodiment of a clamping mechanism attached to a frame and in an unsecured configuration.
Figure 2:
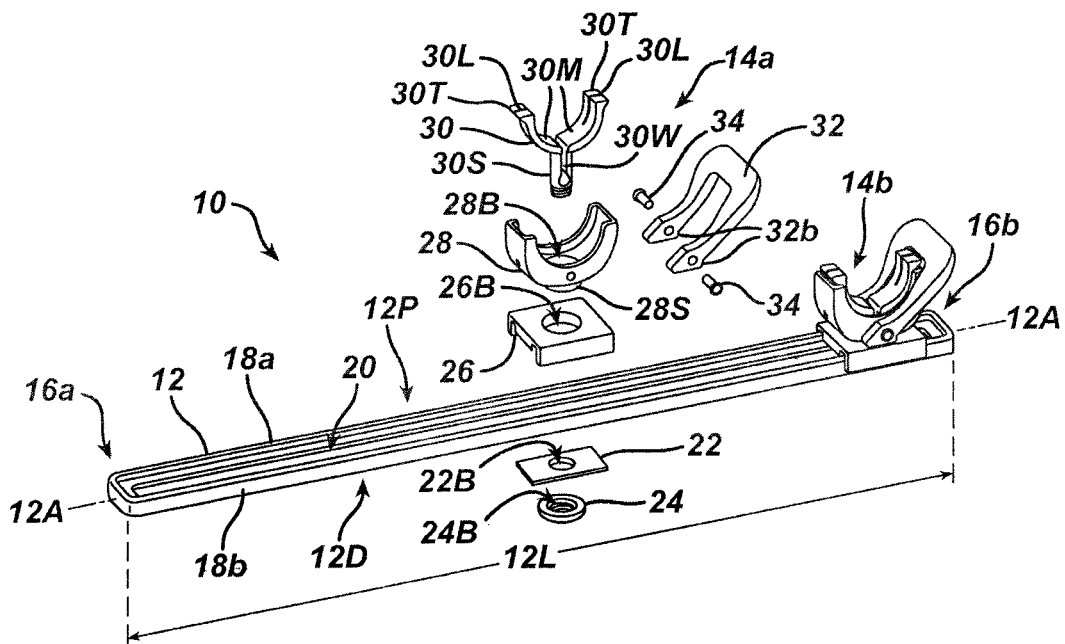
FIG. 2 is an exploded view of the clamping mechanism of FIG. 1 and the frame of FIG. 1 having a second clamping mechanism attached to the frame in an unsecured configuration.

In an exemplary embodiment, shown in FIGS. 1 and 2, a surgical device 10 includes a frame 12 and first and second clamping mechanisms 14a, 14b coupled to the frame 12. Although two clamping mechanisms 14a, 14b are shown coupled to the frame 12, a person skilled in the art will appreciate that any number of clamping mechanisms, same or different from one another, can be attached to the frame 12. Generally, the device 10 can be configured to connect one or more surgical instruments and, if connected to multiple surgical instruments, to facilitate cooperative movement of the surgical instruments. In an exemplary embodiment the device 10 can connect one or more surgical instruments for manipulating a vertebra, as discussed further below, although a person skilled in the art will appreciate that the device 10 can be used to connect any type of spinal or surgical instruments.

The frame 12 and the clamping mechanisms 14a, 14b can each have a variety of sizes, shapes, and configurations. The frame 12 and the clamping mechanisms 14a, 14b can be formed of any one or more materials, same or different from material(s) used to form any other of the frame 12 and clamping mechanisms 14a, 14b. In an exemplary embodiment the device 10 is formed of one or more biocompatible, substantially rigid materials such as metal alloys, stainless steel, titanium, polymers, and ceramics.

As in the illustrated embodiment, the frame 12 can include an elongate bar or rod having opposed first and second ends 16a, 16b with opposed first and second sidewalls 18a, 18b extending therebetween. The opposed ends 16a, 16b can each be curved, as shown, to help prevent the frame 12 from snagging on or otherwise damaging the surgical site or other surgical instruments. The sidewalls 18a, 18b can define a channel, slot, or slit 20, generally referred to as a "channel," extending through the frame 12 and between the sidewalls 18a, 18b along a longitudinal axis 12A and a longitudinal length 12L of the frame 12 between the opposed ends 16a, 16b such that the frame 12 has an elongate o-shape. In another exemplary embodiment, a channel can extend along a partial longitudinal length of the frame 12 such that the clamping mechanisms 14a, 14b can only move along a partial longitudinal length of the frame 12. In yet another exemplary embodiment, the frame 12 can include a plurality of channels each extending along a partial longitudinal length of the frame 12. One or more clamping mechanisms can be attached to the frame 12 in each of the channels, e.g., one clamping mechanism per channel, for slidable movement therein as discussed further below.

The channel 20 in the illustrated embodiment of FIGS. 1 and 2 is smooth and free of obstructions to allow free slidable movement of the clamping mechanisms 14a, 14b therein, as discussed further below, but the channel 20 can optionally include a textured, frictional surface and/or a plurality of obstructions, e.g., teeth, notches, depressions, etc. configured to allow step or incremental movement of the clamping mechanisms 14a, 14b. In such a case, the clamping mechanisms 14a, 14b can include complementary obstructions, e.g., protrusions configured to engage depressions formed in the sidewalls 18a, 18b and facing the channel 20, such that the clamping mechanisms 14a, 14b are configured to be positioned at a plurality of predefined positions within the channel 20. The channel 20 can additionally or alternatively include one or more stop mechanisms formed therein, e.g., protrusions extending radially inward from one or both of the sidewalls 18a, 18b, and being configured to prevent slidable, longitudinal movement of a clamping mechanism when the clamping mechanism abuts the stop mechanism.

As mentioned above, the clamping mechanisms 14a, 14b can have a variety of sizes, shapes, and configurations and can generally be configured to move along a longitudinal axis 12A of the frame 12 and to attach to a surgical instrument. The clamping mechanisms 14a, 14b in the embodiment shown in FIG. 1 are identical, but a person skilled in the art will appreciate that clamping mechanisms coupled to the frame 12 can be the same or different from any one or more other clamping mechanisms coupled to the frame 12.

The first clamping mechanism 14a can include a base portion and a clamping portion. The base portion can be configured to be selectively positioned and secured at a desired location on the frame 12 along the longitudinal axis 12A of the frame 12 between the first and second ends 16a, 16b of the frame 12. The clamping portion can be disposed opposite the base portion and can be configured to selectively engage a surgical instrument, e.g., an elongate tubular element or elongate shaft, at a desired location along a longitudinal axis of the instrument. The base portion and the clamping portion can be integrally formed, as in the illustrated embodiment of FIGS. 1 and 2, or they can be separable elements. Components of the base portion and the clamping portion of the first clamping mechanism 14a are discussed below as non-limiting examples only, and as will be appreciated by a person skilled in the art, can each include a variety of components.

The first clamping mechanism 14a can include, as shown in the embodiment of FIGS. 1 and 2, a plate 22 positioned distal to a distal side 12D of the frame 12, and a washer or nut 24, generally referred to as a "washer," can be positioned distal to the plate 22. A cam or carriage 26, generally referred to as a "carriage," can be positioned proximal to a proximal side 12P of the frame 12. The plate 22 and the carriage 26 can be configured to be selectively movable relative to the frame 12 such that with the plate 22 and the carriage 26 in a first, unsecured configuration the first clamping mechanism 14a can be longitudinally slidable within the channel 20, and with the plate 22 and the carriage 26 in a second, secured configuration the first clamping mechanism 14a can be longitudinally non-movable at a fixed position along the frame's longitudinal axis 12A. The base portion of the first clamping mechanism 14a in the illustrated embodiment can thus include the washer 24 and the carriage 26, each being configured to contact the frame's sidewalls 18a, 18b and be selectively locked and unlocked the frame's sidewalls 18a, 18b to selectively, respectively, prevent and allow movement of the first clamping mechanism 14a relative to the frame 12 along the frame's longitudinal axis 12A.

The first clamping mechanism 14a can also include an outer shell 28 and an inner shell, yoke, or clamp 30, generally referred to as a "clamp," configured to be proximal to and seated in the outer shell 28. The outer shell 28 can be positioned proximal to the carriage 26, with a distally extending cannulated shaft 28S extending into a bore 26B formed in the carriage 26. A distally extending shaft 30S of the clamp 30 can extend through a bore 28B formed through the outer shell 28, through the carriage's bore 26B, through the frame's channel 20, and into bores 22B, 24B respectively formed in the plate 22 and the washer 24. The washer 24 can be attached to a desired location of the clamp's shaft 30S, e.g., welded to the clamp's shaft 30S during manufacture of the first clamping mechanism 14a, such that the clamp 30 proximally extends a desired distance beyond the frame's proximal side 12P. In this way, the clamp 30 can help nonremovably secure the first clamping mechanism 14a to the frame 12. The plate 22 also helps nonremovably secure the first clamping mechanism 14a to the frame 12 as discussed further below. Although the clamping mechanisms 14a, 14b in this illustrated embodiment are nonremovably attached to the frame 12, as discussed further below, in some embodiments, one or more clamping mechanisms coupled to the frame 12 can be releasably and replaceably attachable to the frame 12. The clamping portion of the first clamping mechanism 14a can thus include the clamp 30 configured to contact a surface of a surgical instrument and to be releasably attached thereto in a fixed position.

The clamp 30 can have a variety of sizes, shapes, and configurations. In the illustrated embodiment, the clamp 30 is substantially c-shaped as defined by arms 30M of the clamp 30 that extend in a proximal direction radially outward from the frame 12. An inner surface of the arms 30M can be configured to engage a corresponding substantially c-shaped surface of the outer shell 28, and an outer surface of the arms 30M can be configured to engage a surgical instrument and attach thereto as discussed further below. To help ensure that the arms 30M can securely hold a surgical instrument, the arms 30M can form an arc equal to or greater than about 180°. In the illustrated embodiment of FIGS. 1 and 2, the arms 30M form a 180° arc of a semi-circle. A person skilled in the art will appreciate that the clamp 30 can have another shape, such as having a closed loop in the form of a circle, an ellipse, a rectangle, etc.

The arms 30M can optionally include a stop mechanism, e.g., protrusions, flared terminal ends 30T, etc., and/or optionally include a gripping feature, e.g., a textured surface, slits 30L, etc., extending along at least a partial longitudinal length of an outer, facing surface the arms 30M. As discussed further below, the stop mechanism can be configured to facilitate seating of the clamp 30 in the outer shell 28, and the gripping mechanism can be configured to facilitate a secure, non-slipping hold of a surgical instrument.

The first clamping mechanism 14a can also include an actuator, e.g., a lever 32 that includes a cam 32b located at terminal ends of the lever 32, configured to selectively lock and unlock the first clamping mechanism 14a to the frame 12. The lever 32 can be movable between two positions corresponding to locked and unlocked configurations of the first clamping mechanism 14a. As shown, the lever 32 can be pivotally attached to the outer shell 30 with two pins 34 on opposed sides of the outer shell 30 and opposed sides of the lever 32. Pivotally moving the lever 32 from an open position, shown in FIGS. 1, 3, and 4, to a closed position, shown in FIGS. 5 and 6, can enable the cam 32b to move the first clamping mechanism 14a from an unsecured, unlocked, or movable configuration, generally referred to as an "unsecured configuration," to a secured, locked, or fixed configuration, generally referred to as a "secured configuration." The lever 32 can be configured to fixedly lock in the secured configuration or can, as in the illustrated embodiment, be configured to be selectively movable any number of times between the closed and open positions to selectively move the first clamping mechanism 14a between the secured and unsecured configurations.

Figure 3:
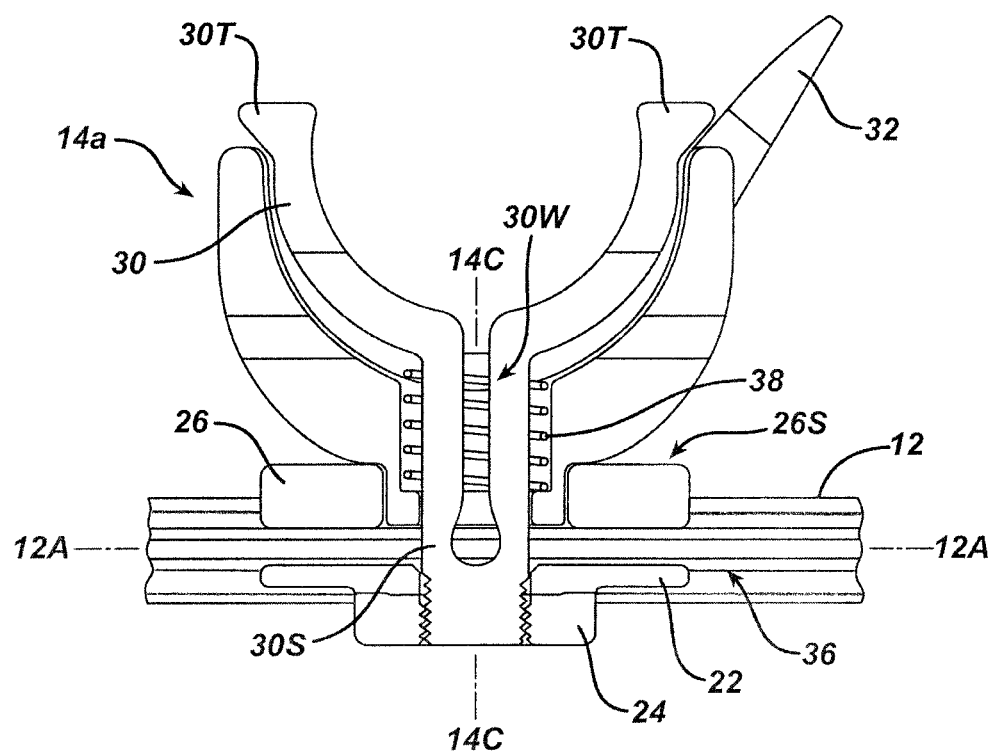
FIG. 3 is a side cross-sectional view of the clamping mechanism of FIG. 1.
Figure 4:
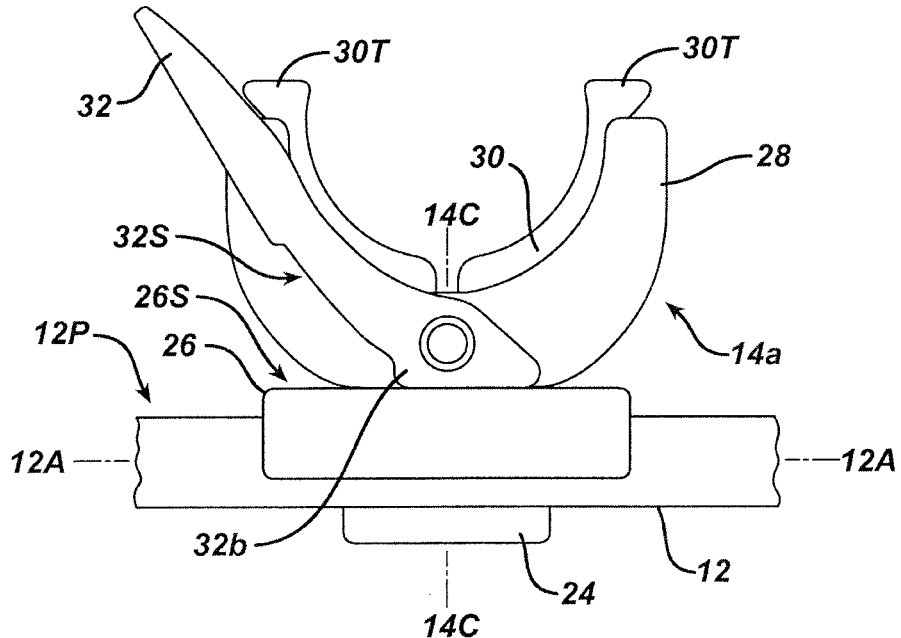
FIG. 4 is a side view of the clamping mechanism of FIG. 1.

In the unsecured configuration, shown in FIGS. 1, 3, and 4, the first clamping mechanism 14a can be configured to be movable relative to the frame 12 in at least one plane. In the illustrated embodiment, the first clamping mechanism 14a is movable in two planes relative to the frame 12. First, the first clamping mechanism 14a can be configured to slide along the frame's longitudinal axis 12A between the frame's opposed ends 16a, 16b to allow adjustment of a horizontal position of the first clamping mechanism 14a. To facilitate slidable movement of the first clamping mechanism 14a, the plate 22 can be seated in a groove, internal channel, or slot 36, generally referred to as a "groove," that can extend along the frame's longitudinal length 12L and can be formed in an inner surface of the sidewalls 18a, 18b facing the channel 20 and also optionally in an inner surface of the opposed ends 16a, 16b facing the channel 20. With the first clamping mechanism 14a in the unsecured configuration, the plate 22 can be configured to be freely slidable within the groove 36. A spring 38 disposed in the bore 28B of the outer shell 28 and disposed around the clamp's shaft 30S can be configured to bias the outer shell 28, and hence also the clamp 30 seated therein, away from, e.g., proximal to, the frame 12. Such outward biasing can help prevent the clamp 30 from interfering with slidable, longitudinal movement of the first clamping mechanism 14a. Second, the first clamping mechanism 14a can be configured to rotate about a central axis 14C of the first clamping mechanism 14a, e.g., a longitudinal axis extending centrally through the clamp's shaft 30S and the first clamping mechanism's various bores 22B, 24B, 26B, 28B, to allow adjustment of clamp's clamping portion relative to a surgical instrument to which it will be attached. The first clamping mechanism's central axis 14C can be substantially perpendicular to the frame's longitudinal axis 12L, as in the illustrated embodiment, which can help allow 360° clockwise and/or counterclockwise rotation of the first clamping mechanism 14a without any interference from the frame 12. In the illustrated embodiment, a portion of the first clamping mechanism 14a is rotatable, e.g., the washer 24, the outer shell 28, the clamp 30, the lever 32, the pins 34, and the spring 36, about the first clamping mechanism's central axis 14C, but in another embodiment an entire clamping mechanism can be configured to rotate about its central axis relative to the frame 12. Although the clamp's shaft 30S has threads formed on its distal end that can engage corresponding threads on the washer 24, the shaft 30S is not threadable relative to the washer 24 except during manufacturing when the washer 24 and the shaft 30S can be threadably adjusted to adjust a proximal distance of the substantially c-shaped clamp 30 from the frame 12 as discussed above. In another embodiment, the clamp's shaft 30S and the washer 24 are not threaded and/or are integrally formed.

In another embodiment, as discussed further below, a clamping mechanism in the unsecured configuration can additionally or alternatively be movable toward and away from the proximal side 12P of the frame 12 in direction substantially perpendicular to the frame's longitudinal axis 12A, which can also allow adjustment of clamp's clamping portion relative to a surgical instrument to which it will be attached.

Figure 5:
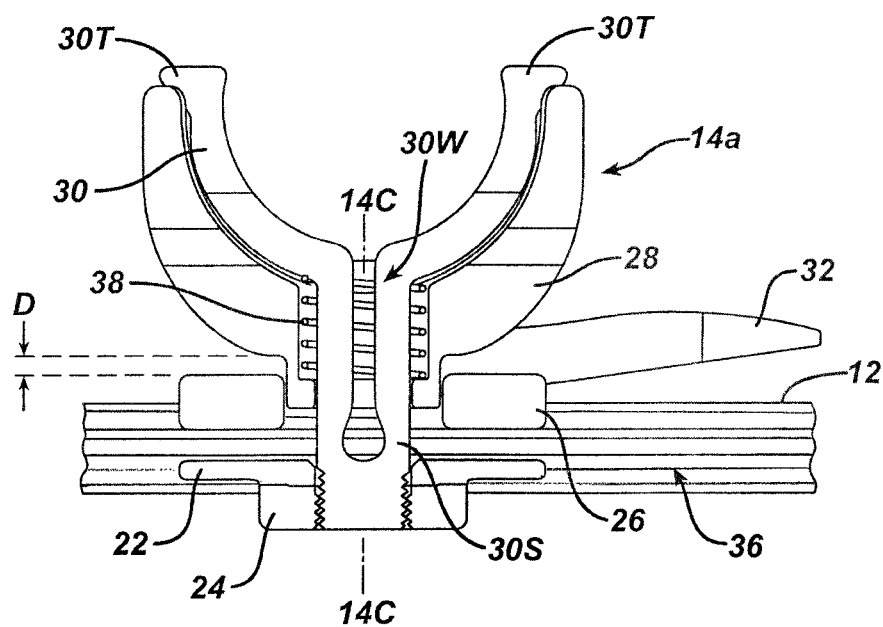
FIG. 5 is a side cross-sectional view of the clamping mechanism of FIG. 1 in a secured configuration.
Figure 6:
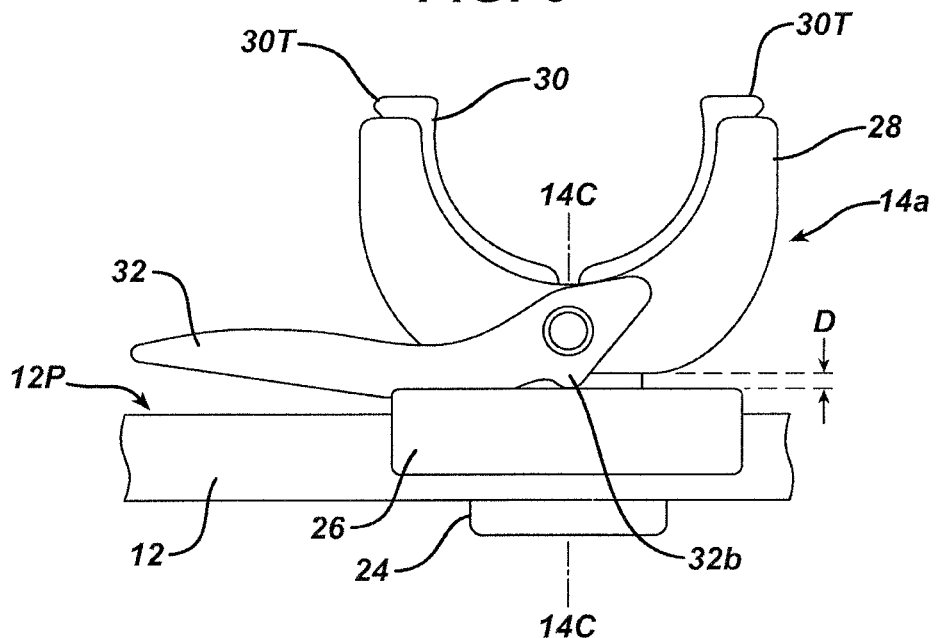
FIG. 6 is a side view of the clamping mechanism of FIG. 5.

In the secured configuration, shown in FIGS. 5 and 6, the first clamping mechanism 14a can be configured to be in a fixed position relative to the frame 12, e.g., no longer be movable in the one or more planes in which the first clamping mechanism 14a was movable in the unsecured configuration. In the secured configuration the clamp 30 of the first clamping mechanism 14a can also be configured to securely hold a surgical instrument as discussed further below.

The first clamping mechanism 14a can be moved between the unsecured and secured configurations by actuating the lever 32, e.g., by pivotally moving the lever 32 about the pins 34 to cause the cam 32b to rotate over an outer surface 26S of the carriage 26. To move the first clamping mechanism 14a from the unsecured configuration to the secured configuration, the lever 32 can be pressed down, e.g., distally toward the proximal side 12P of the frame 12. Similarly, to move the first clamping mechanism 14a from the secured configuration to the unsecured configuration, the lever 32 can be moved up, e.g., proximally away from the proximal side 12P of the frame 12.

As mentioned above, in the secured configuration, the first clamping mechanism 14a can be prevented from moving in the one or more planes of motion in which it was movable in the unsecured configuration. The first clamping mechanism 14a can be prevented from sliding along the frame's longitudinal axis 12A in the secured configuration through movement of the plate 22 to engage a wall of the groove 36 in which it is disposed. Tension between the carriage 26 and the plate 22 with the frame 12 squeezed therebetween can thereby prevent longitudinal translation of the first clamping mechanism 14a along the frame 12. The first clamping mechanism 14a can be prevented from rotating about its central axis 14C in the secured configuration because the lever 32 can have an outer, distal surface 32S configured to engage and correspond in shape to the outer surface 26S of the carriage 26. In this way, the lever 32 can clip around the carriage 26 in the closed position, thereby preventing rotation of the first clamping mechanism 14a relative to the frame 12.

Moving the lever 32, and rotating the cam 32b, to the closed position can also counteract the force provided by the spring 38 and compress the spring 38. Compression of the spring 38 can cause the outer shell 28 to proximally move a distance D away from the outer surface 26S of the carriage 26 which the outer shell 28 can contact when the first clamping mechanism 14a is in the unsecured position. The proximal or upward movement of the outer shell 28 can cause compression of the clamping portion of the clamp 30, e.g., compress the arms 30M together. The flared terminal ends 30T of the clamp 30 can help prevent the outer shell 28 from proximally moving too far and to help compress the arms 30M inward, which can facilitate a strongly grip of a surgical instrument positioned within the substantial c-shape defined by the arms 30M. A well 30W formed in a central portion of the clamp 30 proximally extending through the clamp 30 to a position proximal to a distal end of the clamp 30 can help allow movement of the arms 30M toward one another. The slits 30L in the arms 30M can allow the arms 30M to compensate for any irregularities in an outer surface of the surgical instrument which they are compressed around to hold because each the portions of the arms 30M on either side of the slit 30L can compress a different amount. In the illustrated embodiment the first clamping mechanism 14a is configured to hold a surgical instrument in a fixed position relative to the first clamping mechanism 14a. In another embodiment, a clamping mechanism can be configured to allow polyaxial motion of the surgical instrument when the first clamping mechanism 14a is attached thereto. By way of non-limiting example, a clamping portion of a clamping mechanism can include a partially spherically shaped surface that defines a seat or engagement surface for a surgical instrument, e.g., a partially spherically shaped connection element formed on a shaft of the surgical instrument. Exemplary embodiments of complementary partially spherical shaped elements allowing polyaxial motion of a surgical instrument are described in more detail in U.S. Patent Publication No. 2006/0200132 entitled "Instruments And Methods For Manipulating A Vertebra" filed on Mar. 4, 2005, which is hereby incorporated by reference in its entirety.

Figure 7:
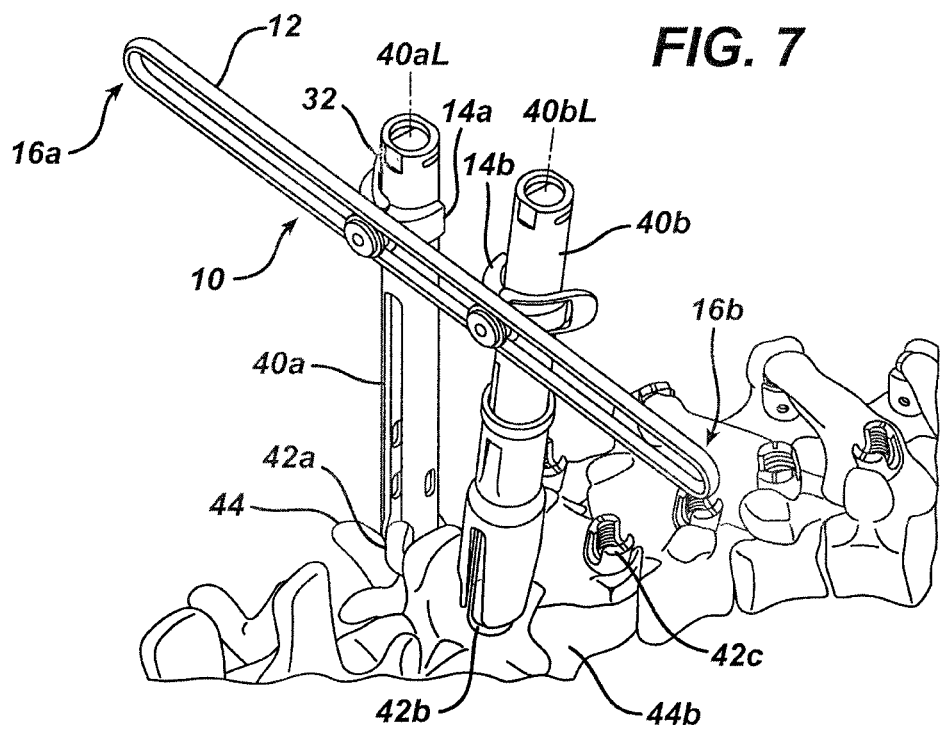
FIG. 7 is a perspective view of the clamping mechanism and frame of FIG. 1 attached to surgical instruments coupled to a vertebra, with an additional clamping mechanism attached to the frame and with each of the clamping mechanisms in secured configurations.

In use, as shown in an exemplary embodiment in FIG. 7, the clamping mechanisms 14a, 14b of the surgical device 10 can be respectively coupled to first and second surgical instruments 40a, 40b respectively attached to first and second bone anchors 42a, 42b inserted in a first vertebra 44. Generally, a size and shape of outer diameters of the first and second surgical instruments 40a, 40b can correspond to a size and shape of the arms of the clamping mechanisms 14a, 14b to allow the clamping mechanisms 14a, 14b to interchangeably attach to the surgical instruments 40a, 40b as discussed above. The first and second surgical instruments 40a, 40b are illustrated as elongate, cylindrical tubular elements having elongate, cylindrical shafts with distal ends configured to releasably engage the bone anchors 42a, 42b. The first surgical instrument 40a in this embodiment has a substantially constant outer diameter along a longitudinal length of its shaft between proximal and distal ends of the first surgical instrument 40a, which can allow the first clamping mechanism 14a, or any other additional or alternative clamping mechanism(s), to grip the first surgical instrument 40a at any location along its longitudinal length. The second surgical instrument 40b in this embodiment has a substantially constant outer diameter along a proximal portion thereof and an enlarged outer diameter along a distal portion thereof. The second clamping mechanism 14b, or any other additional or alternative clamping mechanism(s), can thus grip the second surgical instrument 40b at any location along its longitudinal length in the proximal portion thereof. As will be appreciated by a person skilled in the art, the first and second surgical instruments 40a, 40b can have any size, shape, and configuration, same or different from one another. Exemplary embodiments of surgical instruments are described in more detail in previously mentioned U.S. Patent Publication No. 2006/0200132 entitled "Instruments And Methods For Manipulating A Vertebra" filed on Mar. 4, 2005, and in U.S. Pat. No. 7,179,261 entitled "Percutaneous Access Devices And Bone Anchor Assemblies" issued Feb. 20, 2007, which is hereby incorporated by reference in its entirety.

The illustrated first and second bone anchors 42a, 42b are identical and include elongate threaded shafts (not show) distally extending from a proximal heads having grooves formed therein configured to receive spinal fixation elements (not shown), e.g., spinal rods. However, as will be appreciated by a person skilled in the art, any bone anchors, same or different from one another, configured to engage bone and seat a spinal fixation element can be used in a surgical system including any of the surgical devices described herein. Exemplary embodiments of bone anchors are described in more detail in previously mentioned U.S. Patent Publication No. 2006/0200132 entitled "Instruments And Methods For Manipulating A Vertebra" filed on Mar. 4, 2005 and U.S. Pat. No. 7,179,261 entitled "Percutaneous Access Devices And Bone Anchor Assemblies" issued Feb. 20, 2007, and in U.S. Patent Publication No. 2006/0200131 entitled "Constrained Motion Bone Screw Assembly" filed Mar. 4, 2005, which is hereby incorporated by reference in its entirety.

With both of the first and second clamping mechanisms 14a, 14b being longitudinally translatable along the frame 12, the first and second clamping mechanisms 14a, 14b can be better positioned to attach to the surgical instruments 40a, 40b and the frame 12 can be better positioned for manipulation and for avoiding interference with other aspects of the surgical procedure. Similarly, with both of the first and second clamping mechanisms 14a, 14b being rotatable about their respective central axes, the first and second clamping mechanisms 14a, 14b can be better positioned to attach to surgical instruments 40a, 40b. In this illustrated embodiment, the first clamping mechanism 14a has been rotated about 180° relative to the frame 12 from the position shown in FIG. 1 such that the lever 32 faces the first end 16a of the frame 12 rather than the second end 16b.

When the first and second clamping mechanisms 14a, 14b are at desirable positions relative to the frame 12 and the respective surgical instruments 40a, 40b to which they will be clamped, the levers of the respective first and second clamping mechanisms 14a, 14b can be moved from open positions to closed positions to move the first and second clamping mechanisms 14a, 14b from unsecured positions to secured positions. The first and second clamping mechanisms 14a, 14b can be simultaneously moved from unsecured positions to secured positions or be sequentially moved from unsecured positions to secured positions, with either clamping mechanism 14a, 14b moved first. One of the first and second clamping mechanisms 14a, 14b can be adjusted in the unsecured position and moved to the secured position before the other of the first and second clamping mechanisms 14a, 14b is adjusted in the unsecured position.

With the first and second clamping mechanisms 14a, 14b in secured configurations and attached to the first and second surgical instruments 40a, 40b, respectively, at substantially the same axial position, the frame 12 can be substantially linear such that the frame 12 is substantially perpendicular to the surgical instruments 40a, 40b, as shown in FIG. 7. Because the first and second clamping mechanisms 14a, 14b can be selectively positioned along longitudinal axes 40aL, 40bL of the first and second surgical instruments 40a, 40b, respectively, in another exemplary embodiment the clamping mechanisms 14a, 14b can be positioned at different axial positions such that the frame 12 can be positioned at an angle relative to the surgical instruments 40a, 40b, e.g., with the frame's longitudinal axis 12A and the surgical instruments' longitudinal axes 40aL, 40bL being non-perpendicular. Such varied positioning of the clamping mechanisms 14a, 14b can allow the surgical device 10 to be used with a variety of surgical instruments having different sizes, shapes, and configurations. Additionally, such angled positioning of the frame 12 can facilitate convenient positioning of the frame 12, e.g., to avoid obstructions such as other surgical instruments, to allow improved visibility of a surgical site, etc.

Although the surgical instruments 40a, 40b are inserted in the same vertebra 44 in the embodiment illustrated in FIG. 7, a person skilled in the art will appreciate that the surgical instruments 40a, 40b can be inserted into any number of adjacent or non-adjacent vertebrae. A person skilled in the art will also appreciate that only one surgical device 10 is shown, a plurality of surgical devices 10 can be used to interconnect a plurality of surgical instruments attached to a plurality of bone anchors to create an interconnected system. By way of non-limiting example, a third clamping mechanism (not shown) on a second frame (not shown) can be connected to the first surgical instrument 40a, and a fourth clamping mechanism (not shown) on the second frame can be connected to a third surgical instrument (not shown) connected to a third bone anchor 42c inserted in a second vertebra 44b adjacent to the first vertebra 44. In this way, manipulation of either of the first and second frames and any of the surgical instruments coupled to the first and second frames can effect movement of both the first and second vertebra 44, 44b to which the first and second frames are coupled.

FIGS. 8A-8D and 8G illustrate another exemplary embodiment of a frame 112 and a clamping mechanism 114 having an actuator in the form of a lever 132. In this embodiment, the clamping mechanism 114 includes a T-shaped base portion 115, having the lever 132 coupled to a terminal end thereof, and a substantially c-shaped clamping portion in which a surgical instrument 140 can be side loaded, e.g., advanced through an opening defined by opposed arms 130a, 130b of the clamping mechanism 114 and into a recess 117. Pushing the lever 132 to move the lever 132 from an open position, shown in FIG. 8B, to a closed position, shown in FIGS. 8A, 8C, and 8D, can move the clamping mechanism 114 from an unsecured configuration to a secured configuration similar to that described above.

Figure 8E:
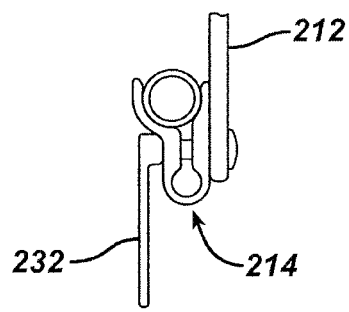
FIG. 8E is a top view of another embodiment of a clamping mechanism attached to a frame with the clamping mechanism in a secured position and coupled to a surgical instrument.
Figure 8F:
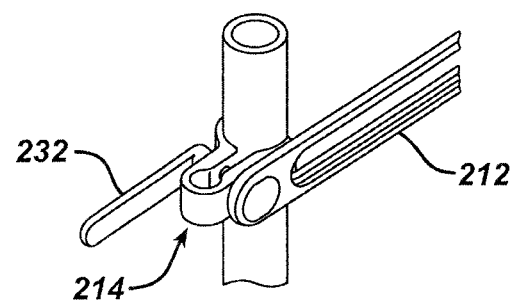
FIG. 8F is a perspective view of the clamping mechanism, frame, and surgical instrument of FIG. 8E.
Figure 8G:
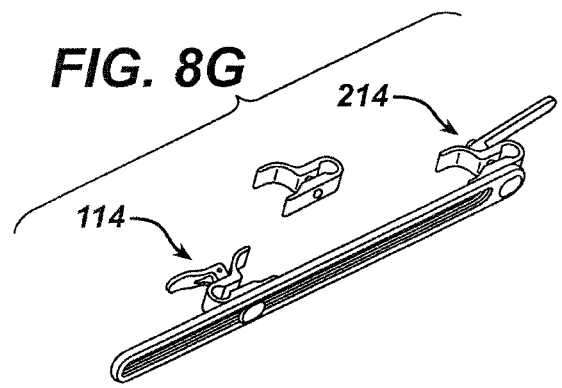
FIG. 8G is a perspective view of the clamping mechanism of FIG. 8A attached to frame and the clamping mechanism of FIG. 8E attached to the frame.

FIGS. 8E-8G illustrate yet another exemplary embodiment of a frame 212 and a clamping mechanism 214 having an actuator in the form of a lever 232. The clamping mechanism 214 is similar to the side loading clamping mechanism 114 of FIGS. 8A-8D. In this embodiment, the lever 232 can be actuated by twisting or rotating the lever 232 rather than through push-pull movement. Twisting the lever 232 in a first direction, e.g., clockwise, can move the clamping mechanism 214 from the unsecured configuration to the secured configuration, while twisting the lever 232 in a second, opposite direction, e.g., counterclockwise, can move the clamping mechanism 214 from the secured configuration to the unsecured configuration.

Figure 9:
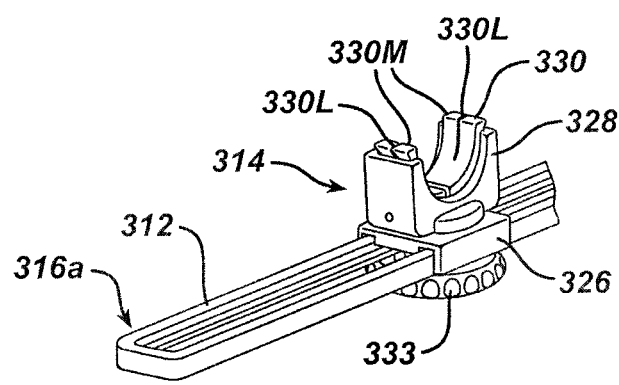
FIG. 9 is a perspective view of another embodiment of a clamping mechanism attached to a frame in an unsecured configuration.
Figure 10:
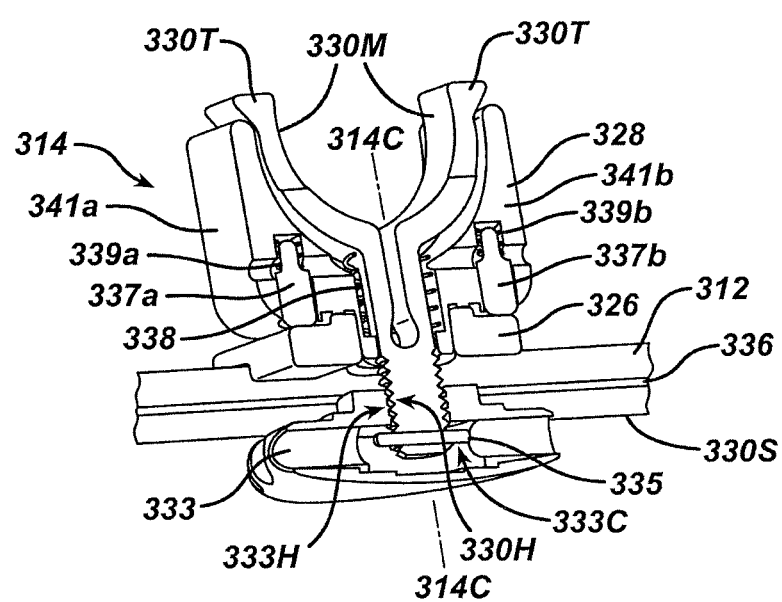
FIG. 10 is a perspective, cross-sectional view of the clamping mechanism and frame of FIG. 9.

In another exemplary embodiment, shown in FIGS. 9 and 10, a clamping mechanism 314 nonremovably attached to a frame 312. The frame 312, as well as other frames described herein, can be configured and used similar to the frame 12 of FIGS. 1-7 discussed above. The clamping mechanism 314 can generally be configured and used similar to the first clamping mechanism 14a of FIGS. 1-7 discussed above. Similar to the first clamping mechanism 14a of FIGS. 1-7, the clamping mechanism 314 includes a carriage 326, an outer shell 328, a spring 338, and a substantially c-shaped clamp 330 having a slit 330L formed in arms 330M thereof with the arms 330M having flared terminal ends 330T. However, in this embodiment, the clamping mechanism 314 includes an actuator in the form of a rotatable knob 333. The knob 333 can be configured to rotate in a first direction, e.g., clockwise, to move the clamping mechanism 314 from a secured configuration to an unsecured configuration, and in a second, opposite direction, e.g., counterclockwise, to move the clamping mechanism 314 from the unsecured configuration to the secured configuration.

In the illustrated embodiment, a shaft 330S of the clamp 330 includes threads 330H in a distal portion thereof similar to the shaft 30S of the clamp 30 in FIGS. 1-7, but in this embodiment the shaft's threads 330H can engage and rotate within corresponding threads 333H formed in the knob 330. In this way, the knob 330 can rotate relative to the clamp 330 around a central axis 314C of the clamping mechanism 314 to move the clamping mechanism 314 between unsecured and secured configurations. The clamping mechanism 314 can include a locking mechanism, e.g., a stop bar, nut, washer, or plate 335, generally referred to as a "stop nut," disposed at a distal end of the shaft 330S and contained within a cavity 333C in the knob 333. The locking mechanism can be configured to nonremovably secure the knob 333 to the shaft 330S. When the knob 333 is moved to an open position by rotating distally or down, e.g., away from the frame 312, the stop nut 335 can engage a proximal surface of the cavity 333C to prevent further distal movement of the knob 333. Similarly, when the knob 333 is moved to a close position by rotating proximally or up, e.g., toward the frame 312, the stop nut 335 can engage a distal surface of the cavity 333C to prevent further proximal movement of the knob 333. The stop nut 335 can have a diameter larger than a diameter of a bore in the knob 333 through which the shaft 330S extends, thereby preventing the stop nut 335 from passing into the bore and failing to lock the knob 333 to the shaft 330S.

In the unsecured configuration, the clamping mechanism 314 can be configured to be movable relative to the frame 312 in at least one plane, as discussed above regarding the first clamping mechanism 14a. As in the illustrated embodiment, the clamping mechanism 314 can be configured to slide along the frame's longitudinal axis between the frame's opposed first end 316a and second end (not shown). A proximal portion of the knob 333 can be configured and used similar to the plate 22 of the first clamping mechanism 14a and be configured to longitudinally slide in a groove 336 formed in the frame 312 when the clamping mechanism 314 is in the unsecured position. The clamping mechanism 314, e.g., each portion of the clamping mechanism 314 except the carriage 326, in the unsecured configuration can also be configured to rotate about the central axis 314C of the clamping mechanism 314.

In the secured configuration, the clamping mechanism 314 can be prevented from moving in the one or more planes of motion in which is was movable in the unsecured configuration, also as discussed above regarding the first clamping mechanism 14a. In the embodiment of FIGS. 9 and 10, the clamping mechanism 314 can be prevented from sliding along the frame's longitudinal axis in the secured configuration through movement of the proximal portion of the knob 333 to engage a wall of the groove 336 in which it is disposed. Tension between the carriage 326 and proximal portion of the knob 333 with the frame 312 squeezed therebetween can thereby prevent longitudinal translation of the clamping mechanism 314 along the frame 312. The clamping mechanism 314 can be prevented from rotating about its central axis 314C in the secured configuration because a pair of springs 337a, 337b disposed in opposed arms 341a, 341b of the outer shell 328 can be compressed, thereby moving a pair of pins 337a, 337b respectively associated with the springs 337a, 337b such that the clamping mechanism 314 cannot rotate. In the unsecured position, the pair of springs 339a, 339b can be in uncompressed positions such that the pins 337a, 337b do not prevent rotation of the clamping mechanism 314.

Figure 11:
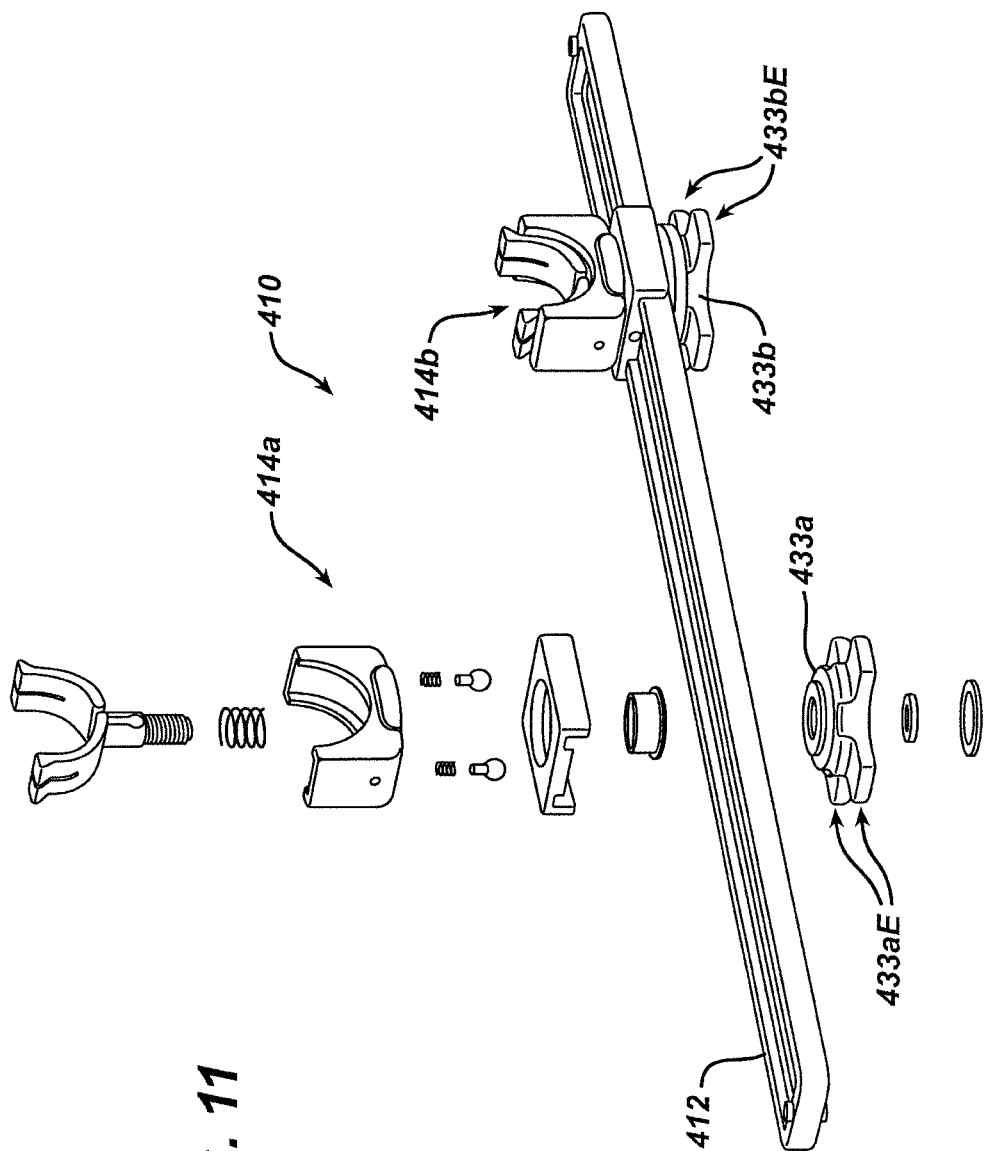
FIG. 11 is an exploded view of another embodiment of a clamping mechanism attached to a frame and a second clamping mechanism attached to the frame.

FIG. 11 illustrates another exemplary embodiment of a surgical device 410 including a frame 412 and first and second clamping mechanisms 414a, 414b coupled to the frame 412. The first and second clamping mechanisms 414a, 414b can generally be configured and used similar to the clamping mechanism 314 of FIGS. 9 and 10. However, in this illustrated embodiment, rotatable knobs 433a, 433b of the first and second clamping mechanisms 414a, 414b have cross-shapes such that the knobs 433a, 433b each include a plurality of extensions 433aE, 433bE configured to ease turning of the knobs 433a, 433b. Although the knobs 433a, 433b each include four rectangular-shaped extensions 433aE, 433bE, a person skilled in the art will appreciate that the knobs 433a, 433b can have any shape and any number of extensions having any shape same or different from any other extension.

As mentioned above, a surgical device can include one or more modular clamping mechanisms configured to be releasably and replaceably coupled to a frame. Allowing clamping mechanisms to be selectively attached to a frame in any number can provide flexibility in a surgical procedure. A minimum number of necessary clamping mechanisms can be selectively attached to the frame to reduce clutter. A surgical kit can be provided that includes at least one frame and a plurality of different modular clamping mechanisms configured to be attached to the at least one frame, thereby allowing selection of modular clamping mechanisms of different sizes, shapes, and configurations for attachment to the frame as desired for particular surgical applications. The surgical kit can optionally include one or more spinal fixation elements, one or more bone anchors, one or more surgical instruments configured to be clamped by the modular clamping mechanisms, and/or other surgical tools. At least one of the frames provided with the kit can have one or more pre-attached clamping mechanisms attached thereto, the pre-attached clamping mechanisms being modular, non-removable from the frame but movable relative thereto between secured and unsecured configurations, and/or non-removable from the frame and not movable relative thereto.

FIGS. 12-16 illustrate a modular surgical device 510 including an actuator in the form of a cross-shaped rotatable knob 533 and can be configured and used similar to the device 410 of FIG. 11. Although only one clamping mechanism 514 is illustrated in FIGS. 12-16, a person skilled in the art will appreciate that any number of modular clamping mechanisms can be attached to a frame 512 and that any number of modular clamping mechanisms can be attached to a frame coupled to any number of nonremovable clamping mechanisms.

The modular clamping mechanism 514 includes a carriage 526 similar to other carriages described herein, but the illustrated modular clamping mechanism's carriage 526 include a hinge 527 on one side 526a thereof and a depression 529 on an opposite side 526b thereof. The hinge 527 can have a variety of sizes, shapes, and configurations, as will be appreciated by a person skilled in the art, and can be integral with the carriage 526, as shown in the illustrated embodiment, or it can be a separate component. A person skilled in the art will also appreciate that the depression 529 formed in the carriage 526 can also have a variety of sizes, shapes, and configurations and can, in another exemplary embodiment, be an opening formed through a side of the carriage 526 rather than a depression indented therein.

The modular clamping mechanism 514 also includes a plate 522 similar to other plates described herein, but the illustrated modular clamping mechanism's plate 522 is attached to the carriage 526 via the hinge 527 and a closure mechanism, e.g., a latch 531, hingedly attached to one side of the plate 522 and receivable in the depression 529 formed in the carriage. The latch 531 is shown in the illustrated embodiment as a separate component from the plate 522 but hingedly secured thereto, but the latch 531 can be integrally formed with the plate 522. Moreover, the latch 531 can instead be integrally formed with the carriage 526 or hingedly secured thereto. Similarly, the hinge 527 can be integrally formed with the plate 522 rather than with the carriage 526. As in the illustrated embodiment, the hinge 527 can be fixedly, hingedly connected to one side 522b of the plate 522 with a first pin 543a, and the latch 531 can be fixedly, hingedly connected to an opposite side 522a thereof with a second pin 543b. A third pin 543c can be used to help attach the plate 522 to the knob 533.

Figure 12:
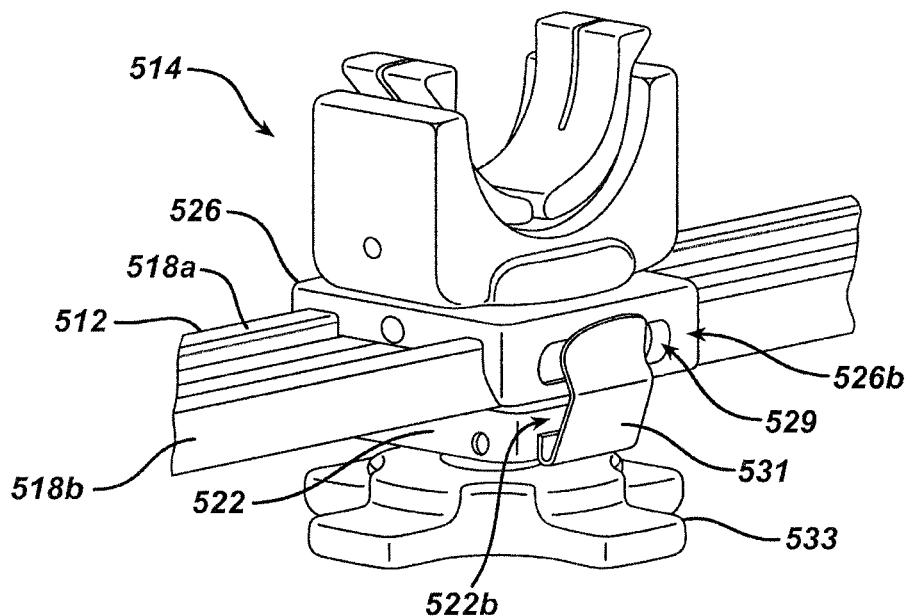
FIG. 12 is a perspective view of one embodiment of a modular clamping mechanism attached to a frame in an unsecured configuration.
Figure 13:
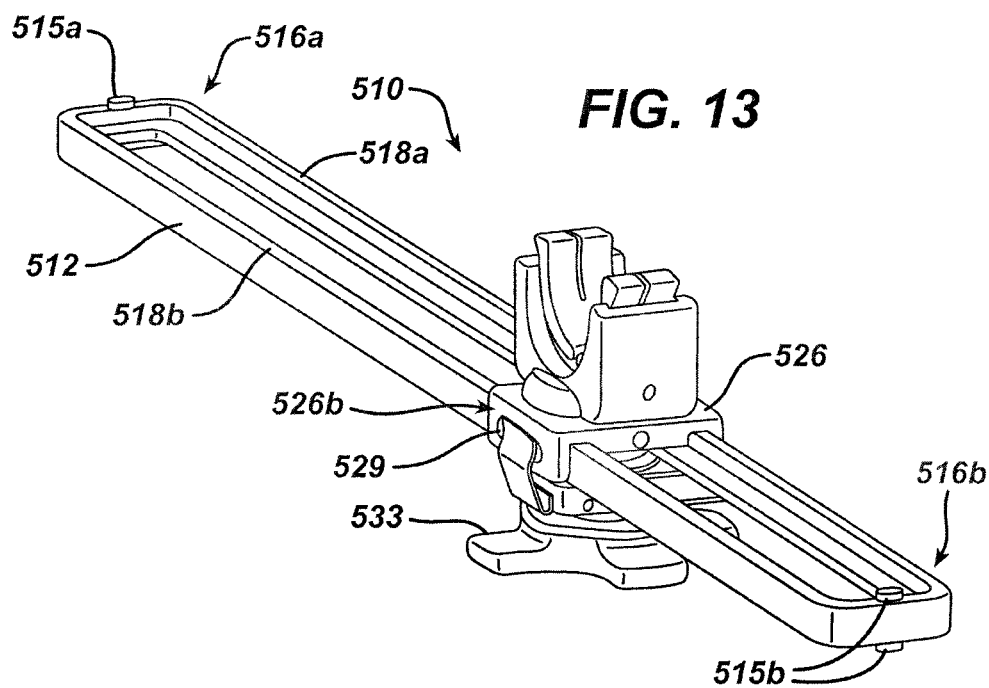
FIG. 13 is another perspective view of the modular clamping mechanism and frame of FIG. 12.
Figure 14:
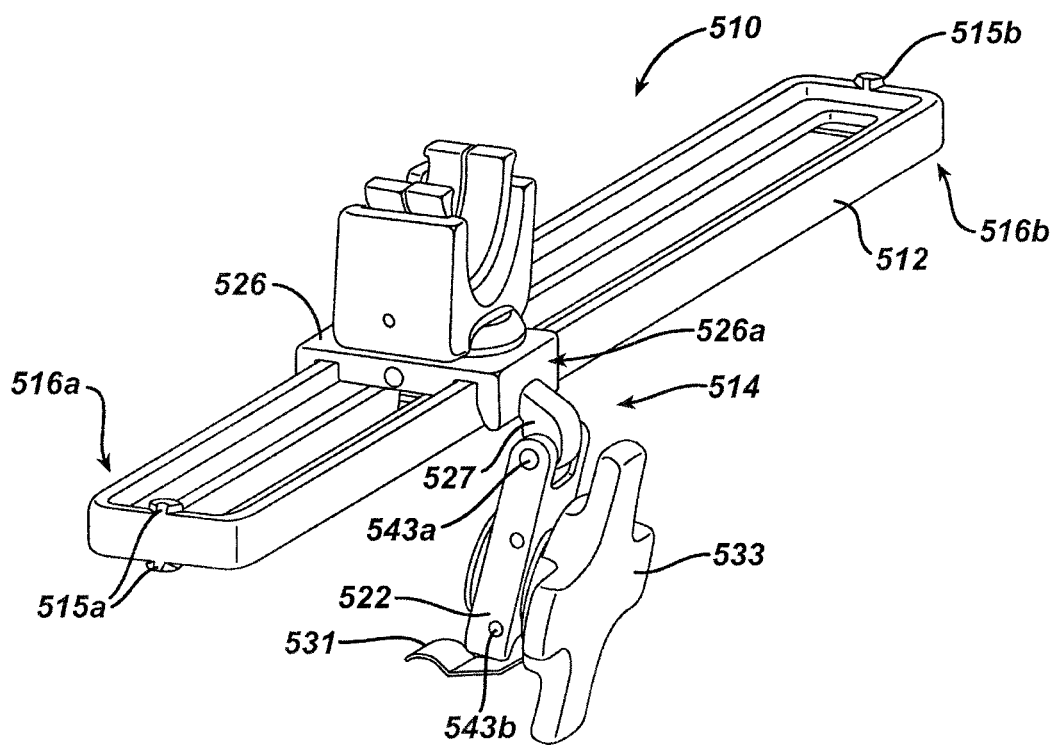
FIG. 14 is a perspective view of the modular clamping mechanism of FIG. 12 in an open configuration and unattached to the frame.
Figure 15:
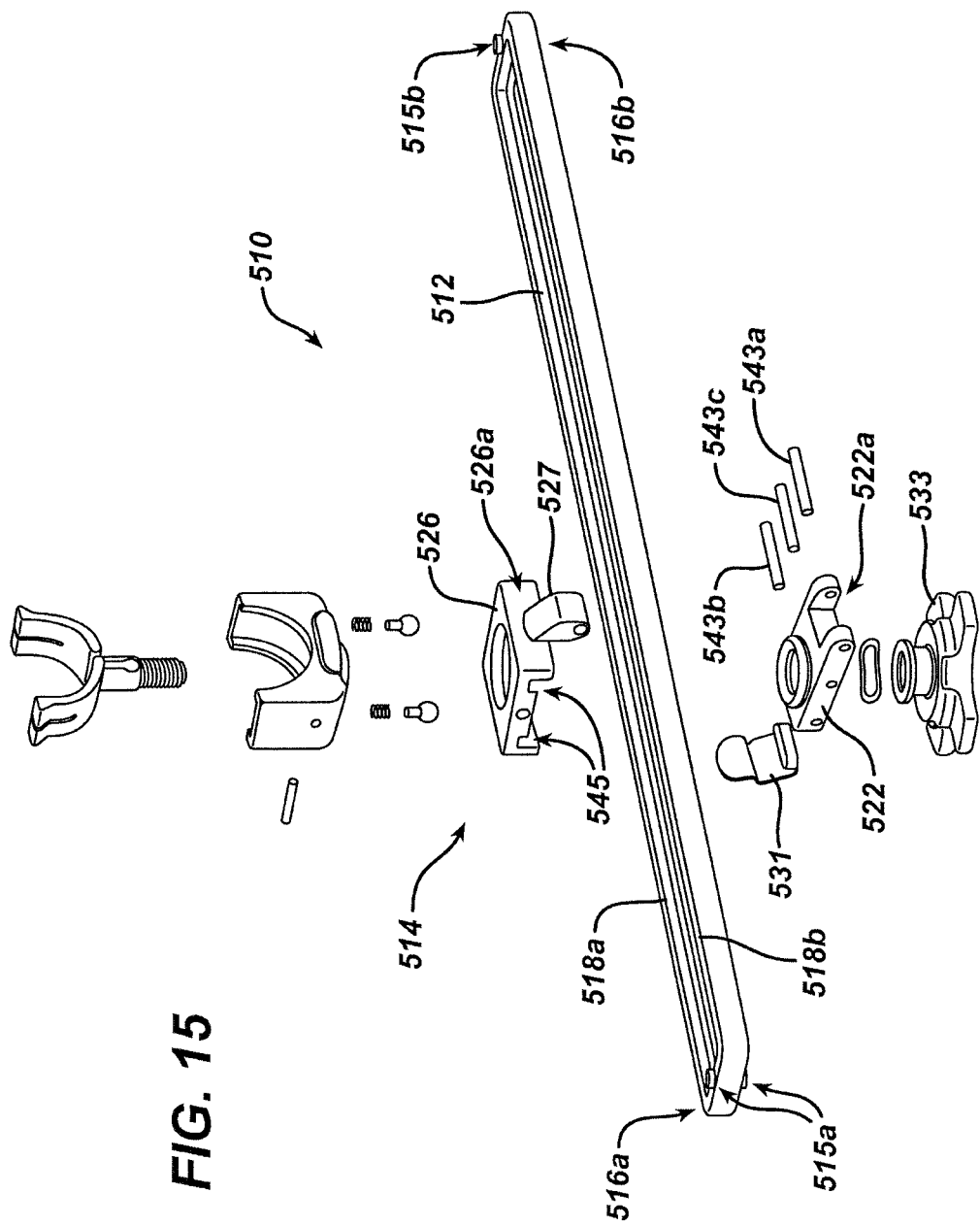
FIG. 15 is an exploded view of the modular clamping mechanism of FIG. 12 and the frame of FIG. 12.
Figure 16:
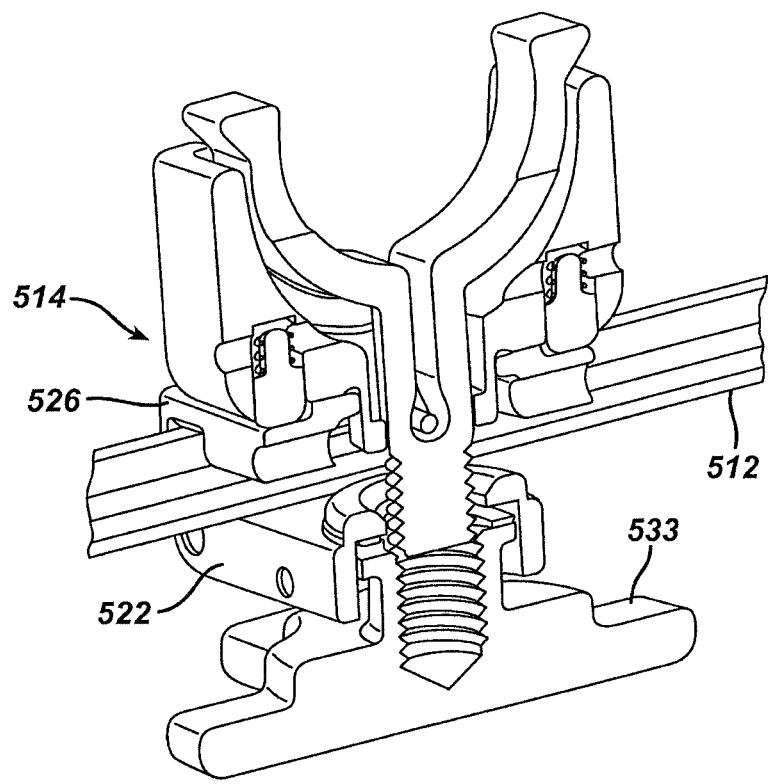
FIG. 16 is a perspective, cross-sectional view of the modular clamping mechanism and frame of FIG. 12.

With the modular clamping mechanism 514 in an open or unattached configuration, as shown in FIG. 14, the modular clamping mechanism 514 is free to be attached to the frame 512 or removed from the frame 512. To attach the modular clamping mechanism 514 to the frame 512, the modular clamping mechanism 514 can be moved to a closed or attached configuration, as shown in FIGS. 12, 13, and 16, by pivoting the hinge 527 to bring the latch 531 into contact with the depression 529 into which the latch 531 can snap, click, hook, magnetically affix, or otherwise releasably and replaceably attach. In another embodiment, the latch 531 can be configured to fixedly attach to the carriage 526 such that the modular clamping mechanism 514 is not releasable from the frame 512 once the modular clamping mechanism 514 is in the closed configuration positioned around the frame 512. A distal side of the carriage 526 can include opposed channels or grooves 545, generally referred to as "grooves," configured to engage opposed sidewalls 518a, 518b of the frame 512. Aligned the opposed grooves 545 with the opposed sidewalls 518a, 518b can help ensure proper alignment of the modular clamping mechanism 514 relative to the frame 512. As a default, the modular clamping mechanism 514 can be attached to the frame 512 in the unsecured configuration, e.g., configured to move relative to the frame 512.

Once the modular clamping mechanism 514 is in the closed configuration and positioned around the frame 512, the modular clamping mechanism 514 can be moved between secured and unsecured configurations, similar to that discussed above.

The frame 512 can optionally include one or more stop mechanisms 515a, 515b at opposed first and second ends 516a, 516b of the frame 512 to prevent the modular clamping mechanism 514, and/or any other clamping mechanisms attached to the frame 512, from sliding off either end 516a, 516b of the frame 512. The stop mechanisms 515a, 515b are shown as singular protrusions extending in a substantially perpendicular direction from proximal and distal side 512P, 512D, but the frame 512 can include any number of stop mechanisms 515a, 515b having any size, shape, and configuration. The stop mechanisms 515a, 515b are identical in the illustrated embodiment but can be different from one another.

Figure 17:
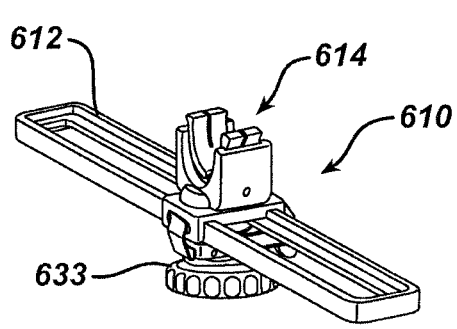
FIG. 17 is a perspective view of another embodiment of a modular clamping mechanism in a closed configuration and attached to a frame.
Figure 18:
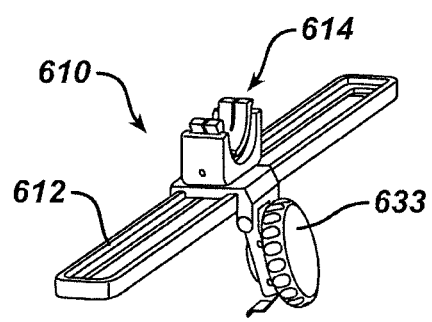
FIG. 18 is a perspective view of the modular clamping mechanism of FIG. 17 in an open configuration and unattached to the frame.

FIGS. 17 and 18 illustrate another exemplary embodiment of a surgical device 610 including a frame 612 and a modular clamping mechanism 614 coupled to the frame 612. The modular clamping mechanism 614 can generally be configured and used similar to the modular clamping mechanism 514 of FIGS. 12-16, but instead of having a cross-shaped knob, the modular clamping mechanism 614 includes a circular, disc-shaped knob 633 similar to the knob 333 of FIGS. 9 and 10.

Figure 19:
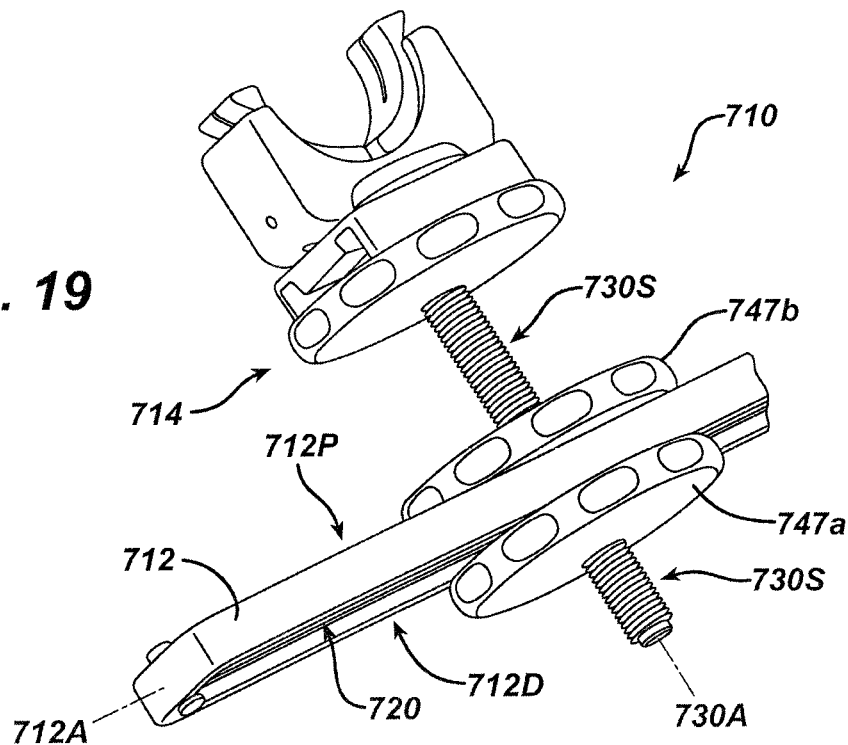
FIG. 19 is a perspective view of one embodiment of a depth-adjusting clamping mechanism attached to a frame.

As mentioned above, a clamping mechanism attached to a frame can be configured to have an adjustable depth such that the clamping mechanism can be movable toward and away from a side of the frame in direction substantially perpendicular to the frame's longitudinal axis. FIG. 19 illustrates one embodiment of a surgical device 710 including a depth-adjustable clamping mechanism 714 attached to a frame 712. The depth-adjustable clamping mechanism 714 can be configured and used similar to the clamping mechanism 314 of FIGS. 9 and 10, but a clamp 730 of the depth-adjustable clamping mechanism 714 can include a shaft 730S that extends through a circular, disc-shaped rotatable knob 733 rather than terminating within the knob 733 as in the embodiment of FIGS. 9 and 10. The clamp's shaft 730S can be threaded in at least a distal portion thereof and be positioned through a channel 720 of the frame 712 such that a longitudinal axis 730A of the shaft 730S is substantially perpendicular to a longitudinal axis 712A of the frame 712. First and second rotatable knobs 747a, 747b can be threaded onto the shaft 730S on opposed sides 712D, 712P of the frame 712. With the first and second rotatable knobs 747a, 747b tightened against the frame's opposed sides 712D, 712P, the depth-adjustable clamping mechanism 714 can be held in a fixed depth position relative to the frame 712. The knobs 747a, 747b can be selectively loosened and tightened to adjust a position of the shaft 730S through the frame 712 and thus a depth of the depth-adjustable clamping mechanism 714 relative to the frame 712.

Figure 20:
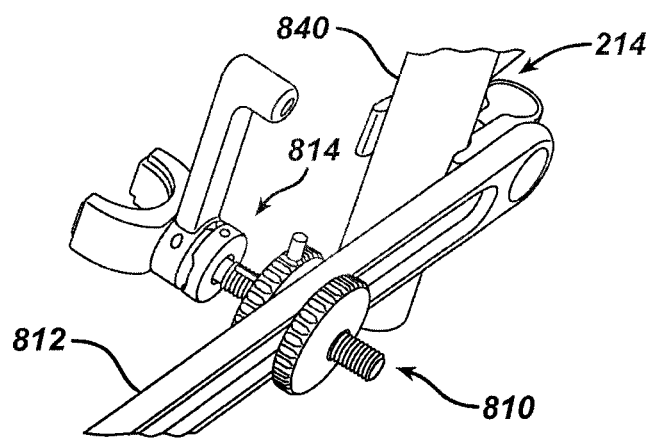
FIG. 20 is a perspective view of another embodiment of a depth-adjusting clamping mechanism attached to a frame with the clamping mechanism of FIG. 8E attached to the frame and clamping a surgical instrument.

FIG. 20 illustrates another exemplary embodiment of a surgical device 810 including a frame 812 and a depth-adjustable clamping mechanism 814 coupled to the frame 812. The depth-adjustable clamping mechanism 814 can generally be configured and used similar to the depth-adjustable clamping mechanism 714 of FIG. 19. FIG. 20 also illustrates the clamping mechanism 214 of FIGS. 8E-8G clamping a surgical instrument 840.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a housing, a proximal retractor base, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the methods, devices, and systems disclosed herein based on the above-described embodiments. Accordingly, the methods, devices, and systems disclosed herein are not to be limited by what has been particularly shown and described, except as indicated by the appended claims. All publications and references cited herein are expressly incorporated herein by reference in their entirety.

The invention claimed is:

1. A surgical device, comprising:
a frame having a through-hole formed therein that extends longitudinally along a length of the frame; and
a clamping mechanism mounted to the frame such that a portion of the clamping mechanism extends through the through-hole and such that the clamping mechanism can be positioned at any of a plurality of locations along the length of the frame, the clamping mechanism being movable between an unsecured configuration in which the clamping mechanism is free to move along the length of the frame and a secured configuration in which the clamping mechanism cannot move along the length of the frame, the clamping mechanism including:
a carriage,
a plate connected to the carriage by a hinge, the plate being pivotable relative to the carriage to selectively capture the frame between the carriage and the plate, and
a clamp configured to engage an instrument disposed therein when the clamping mechanism is in the secured configuration.

2. The device of claim 1, wherein the plate includes a latch that engages the carriage to prevent the plate from pivoting relative to the carriage.

3. The device of claim 1, wherein the clamp is disposed in an outer shell, the clamp having two opposed arms that move toward one another when the clamping mechanism moves from the unsecured configuration to the secured configuration by movement of the arms with respect to the outer shell.

4. The device of claim 3, further comprising a rotatable knob threadably mated to the clamp and configured to urge the clamp against the outer shell to move the arms of the clamp toward one another.

5. The device of claim 1, wherein the carriage includes first and second grooves in which opposed sidewalls of the frame are slidably disposed.

6. The device of claim 1, wherein the clamping mechanism is rotatable about a central axis of the clamping mechanism in the unsecured configuration.

7. The device of claim 1, wherein the frame further comprises a stop that prevents the clamping mechanism from sliding off the frame.

8. The device of claim 7, wherein the stop comprises a first stop and a second stop, the first and second stops located at opposite ends of the frame.

9. A surgical device, comprising:
- a frame having an upper surface, a lower surface, first and second opposed end surfaces, and first and second opposed side surfaces, the frame having a channel that extends longitudinally along at least a portion of the frame;
- a clamping mechanism slidably mounted to the frame and selectively movable between a secured configuration and an unsecured configuration, the clamping mechanism including:
  - a clamp having opposed arms positioned within an outer shell, the opposed arms being configured to clamp an instrument disposed therebetween when the clamping mechanism is in the secured configuration;
  - a first rotatable knob threadably coupled to the clamp to pull the clamp into engagement with the outer shell,
- wherein the clamping mechanism is movable toward and away from the upper surface of the frame in a direction perpendicular to a longitudinal axis of the frame, and
- wherein the clamp includes a threaded shaft that extends through the first rotatable knob, and second and third rotatable knobs threadably mounted to the shaft.

10. The device of claim 9, wherein the threaded shaft extends through the second and third knobs.

11. The device of claim 9, wherein the second rotatable knob abuts the upper surface of the frame and the third rotatable knob abuts the lower surface of the frame.

12. The device of claim 9, wherein the second and third rotatable knobs are movable along the length of the shaft to move the clamping mechanism toward or away from the frame.

* * * * *